United States Patent [19]

Zones et al.

[11] Patent Number: 4,910,006

[45] Date of Patent: Mar. 20, 1990

[54] ZEOLITE SSZ-26

[75] Inventors: Stacey I. Zones, San Francisco; Donald S. Santilli, Larkspur; James N. Ziemer, Hercules; Dennis L. Holtermann, Crockett; Theresa A. Pecoraro, Danville; Robert A. Innes, San Rafael, all of Calif.

[73] Assignee: Chevron Research Company, San Francisco, Calif.

[21] Appl. No.: 172,737

[22] Filed: Mar. 23, 1988

[51] Int. Cl.[4] .............................................. C01B 33/28
[52] U.S. Cl. ..................................... 423/328; 423/326; 423/593; 423/594; 423/600; 423/618; 502/64; 502/71
[58] Field of Search ............... 423/328 C, 328 T, 326, 423/600, 618, 594, 593; 502/64, 71

[56] References Cited

U.S. PATENT DOCUMENTS

| 4,372,930 | 2/1983 | Short et al. | 423/324 |
|---|---|---|---|
| 4,508,837 | 4/1985 | Zones | 502/62 |
| 4,544,538 | 10/1985 | Zones | 423/326 |
| 4,610,854 | 9/1986 | Zones | 423/326 |

OTHER PUBLICATIONS

Helv. Chim Acta, (1974), vol. 57, p. 1533, Sieber et al.
Merck Index (10th Ed.), 1983, p. 1316.

Primary Examiner—John Doll
Assistant Examiner—Stuart L. Hendrickson
Attorney, Agent, or Firm—T. G. De Jonghe; V. J. Cavalieri

[57] ABSTRACT

A crystalline zeolite SSZ-26 is prepared using a hexamethyl [4.3.3.0] propellane-8,11-diammonium cation as a template. Also disclosed is a process for converting hydrocarbons with crystalline zeolite SSZ-26.

12 Claims, No Drawings

ZEOLITE SSZ-26

BACKGROUND OF THE INVENTION

Natural and synthetic zeolitic crystalline aluminosilicates are useful as catalysts and adsorbents. These aluminosilicates have distinct crystal structures which are demonstrated by X-ray diffraction. The crystal structure defines cavities and pores which are characteristic of the different species. The adsorptive and catalytic properties of each crystalline aluminosilicate are determined in part by the dimension of its pores and cavities. Thus, the utility of a particular zeolite in a particular application depends at least partly on its crystal structure.

Because of their unique molecular sieving characteristics, as well as their catalytic properties, crystalline aluminosilicates are especially useful in such applications as gas drying and separation and hydrocarbon conversion. Although many different crystalline aluminosilicates and silicates have been disclosed, there is a continuing need for new zeolites and silicates with desirable properties for gas separation and drying, hydrocarbon and chemical conversions, and other applications.

Crystalline aluminosilicates are usually prepared from aqueous reaction mixtures containing alkali or alkaline earth metal oxides, silica, and alumina. "Nitrogenous zeolites" have been prepared from reaction mixtures containing an organic templating agent, usually a nitrogen-containing organic cation. By varying the synthesis conditions and the composition of the reaction mixture, different zeolites can be formed using the same templating agent. Use of N,N,N-trimethyl cyclopentylammonium iodide in the preparation of Zeolite SSZ-15 molecular sieve is disclosed in U.S. Pat. No. 4,610,854; use of 1-azoniaspiro [4.4] nonyl bromide and N,N,N-trimethyl neopentylammonium iodide in the preparation of a molecular sieve termed "Losod" is disclosed in Helv. Chim. Acta (1974), Vol. 57, page 1533 (W. Sieber and W. M. Meier); use of quinuclidinium compounds to prepare a zeolite termed "NU-3" is disclosed in European Patent Publication No. 40016; use of 1,4-di(1-azoniabicyclo [2.2.2.]octane) lower alkyl compounds in the preparation of Zeolite SSZ-16 molecular sieve is disclosed in U.S. Pat. No. 4,508,837; use of N,N,N-trialkyl-1-adamantamine in the preparation of zeolite SSZ-13 molecular sieve is disclosed in U.S. Pat. No. 4,544,538.

SUMMARY OF THE INVENTION

We have prepared a family of crystalline aluminosilicate molecular sieves with unique properties, referred to herein as "Zeolite SSZ-26", or simply "SSZ-26", and have found a highly effective method for preparing SSZ-26.

SSZ-26 has a mole ratio of an oxide selected from silicon oxide, germanium oxide, and mixtures thereof to an oxide selected from aluminum oxide, gallium oxide, iron oxide, and mixtures thereof in the range of 10:1 to 200:1, and having the X-ray diffraction lines of Table 1 below. The zeolite further has a composition, as synthesized and in the anhydrous state, in terms of mole ratios of oxides as follows: (0.1 to 2.0)$Q_2O$:(0.1 to 2.0)$M_2O$:$W_2O_3$:(10 to 200)$YO_2$ wherein M is an alkali metal cation, W is selected from aluminum, gallium, iron, and mixtures thereof, Y is selected from silicon, germanium and mixtures thereof, and Q is a hexamethyl [4.3.3.0] propellane-8,11-diammonium cation. SSZ-26 zeolites can have a $YO_2$:$W_2O_3$ mole ratio in the range of 10:1 to 200:1. As prepared, the silica:alumina mole ratio is typically in the range of 12:1 to 100:1. Higher mole ratios can be obtained by treating the zeolite with chelating agents or acids to extract aluminum from the zeolite lattice. This includes reagents such as $(NH_4)_2SiF_6$ or acidic ion exchange resins. The silica:alumina mole ratio can also be increased by using silicon and carbon halides and other similar compounds. Preferably, SSZ-26 is an aluminosilicate wherein W is aluminum and Y is silicon.

Our invention also involves a method for preparing SSZ-26 zeolites, comprising preparing an aqueous mixture containing sources of a hexamethyl [4.3.3.0] propellane-8,11-diammonium cation, an oxide selected from aluminum oxide, gallium oxide, iron oxide, and mixtures thereof, and an oxide selected from silicon oxide, germanium oxide, and mixtures thereof, and having a composition, in terms of mole ratios of oxides, falling within the following ranges: $YO_2$/$W_2O_3$, 10:1 to 200:1; and Q/$YO_2$ 0.05:1 to 0.50:1; wherein Y is selected from silicon, germanium, and mixtures thereof, W is selected from aluminum, gallium, iron, and mixtures thereof, and Q is a hexamethyl [4.3.3.0] propellane-8,11-diammonium cation; maintaining the mixture at a temperature of at least 100° C. until the crystals of said zeolite are formed; and recovering said crystals.

DETAILED DESCRIPTION OF THE INVENTION

SSZ-26 zeolites, as synthesized, have a crystalline structure whose X-ray powder diffraction pattern shows the following characteristic lines:

TABLE 1

| 2 $\theta$ | d/n | I/Io × 100 |
|---|---|---|
| 7.78 | 11.36 | 100 |
| 20.33 | 4.389 | 63 |
| 21.37 | 4.158 | 25 |
| 21.99 | 4.042 | 53 |
| 22.85 | 3.890 | 46 Sh |
| 23.00 | 3.867 | 64 |
| 26.49 | 3.365 | 33 |

Sh = Shoulder

Typical SSZ-26 aluminosilicate zeolites have the X-ray diffraction pattern of Tables 3–7.

The X-ray powder diffraction patterns were determined by standard techniques. The radiation was the K-alpha/doublet of copper and a scintillation counter spectrometer with a strip-chart pen recorder was used. The peak heights I and the positions, as a function of $2\theta$ where $\theta$ is the Bragg angle, were read from the spectrometer chart. From these measured values, the relative intensities, 100I/$I_o$, where $I_o$ is the intensity of the strongest line or peak, and d, the interplanar spacing in Angstroms corresponding to the recorded lines, can be calculated. The X-ray diffraction pattern of Table 1 is characteristic of SSZ-26 zeolites. The zeolite produced by exchanging the metal or other cations present in the zeolite with various other cations yields substantially the same diffraction pattern although there can be minor shifts in interplanar spacing and minor variations in relative intensity. Minor variations in the diffraction pattern can also result from variations in the organic compound used in the preparation and from variations in the silica-to-alumina mole ratio from sample to sample. Calcination can also cause minor shifts in the X-ray diffraction pattern. Notwithstanding these minor perturbations, the basic crystal lattice structure remains unchanged.

After calcination the SSZ-26 zeolites have a crystalline structure whose X-ray powder diffraction pattern shows the following characteristic lines as indicated in Table 2 below:

TABLE 2

| 2 θ | d/n | I/Io × 100 |
|---|---|---|
| 7.78 | 11.36 | 100 |
| 20.22 | 4.392 | 18 |
| 21.34 | 4.164 | 5 |
| 21.98 | 4.044 | 15 |
| 22.93 | 3.878 | 13 Sh |
| 23.08 | 3.853 | 19 |
| 26.48 | 3.366 | 12 |

Sh = Shoulder

SSZ-26 zeolites can be suitably prepared from an aqueous solution containing sources of an alkali metal oxide, a hexamethyl [4.3.3.0] propellane-8,11-diammonium cation, an oxide of aluminum, gallium, iron, or mixtures thereof, and an oxide of silicon or germanium, or mixture of the two. The reaction mixture should have a composition in terms of mole ratios falling within the following ranges:

|  | Broad | Preferred |
|---|---|---|
| $YO_2/W_2O_3$ | 10–200 | 20–100 |
| $OH^-/YO_2$ | 0.10–1.0 | 0.20–0.50 |
| $Q/YO_2$ | 0.05–0.50 | 0.05–0.20 |
| $M^+/YO_2$ | 0.05–0.50 | 0.15–0.30 |
| $H_2O/YO_2$ | 15–300 | 25–60 |
| $Q/Q + M^+$ | 0.20–0.70 | 0.30–0.67 | wherein Q is a hexamethyl [4.3.3.0] propellane-8,11-diammonium cation, Y is silicon, germanium or both, and W is aluminum, gallium, iron, or mixtures thereof. M is an alkali metal ion, preferably sodium. The organic propellane compound which acts as a source of the propellane quaternary ammonium ion employed can provide hydroxide ion. Anions which are associated with the organic cation are those which are not detrimental to the formation of the zeolite.

The hexamethyl [4.3.3.0] propellane-8,11-diammonium cation component Q, of the crystallization mixture, is preferably derived from a compound of the formula:

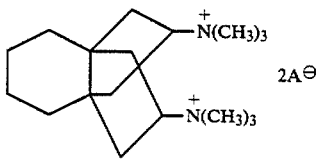

including syn,syn; syn,anti; and anti,anti orientations and wherein $A^\ominus$ is an anion which is not detrimental to the formation of the zeolite. Representative of the anions include halogen, e.g., fluoride, chloride, bromide and iodide, hydroxide, acetate, sulfate, tetrafluoroborate, carboxylate, and the like. Hydroxide is the most preferred anion.

The reaction mixture is prepared using standard zeolitic preparation techniques. Typical sources of aluminum oxide for the reaction mixture include aluminates, alumina, and aluminum compounds such as $AlCl_3$, $Al_2(SO_4)_3$, kaolin clays, and other zeolites. Typical sources of silicon oxide include silicates, silica hydrogel, silicic acid, colloidal silica, fumed silicas, tetraalkyl orthosilicates, and silica hydroxides. Gallium, iron, and germanium can be added in forms corresponding to their aluminum and silicon counterparts. Salts, particularly alkali metal halides such as sodium chloride, can be added to or formed in the reaction mixture. They are disclosed in the literature as aiding the crystallization of zeolites while preventing silica occlusion in the lattice.

The reaction mixture is maintained at an elevated temperature until the crystals of the zeolite are formed. The temperatures during the hydrothermal crystallization step are typically maintained from about 140° C. to about 200° C., preferably from about 150° C. to about 180° C. and most preferably from about 150° C. to about 170° C. The crystallization period is typically greater than 1 day and preferably from about 5 days to about 10 days.

Preferably the zeolite is prepared using mild stirring or agitation. High speed stirring may lead to co-crystallization of at least one other zeolite. Stirring at less than 100 RPM is preferred.

The hydrothermal crystallization is conducted under pressure and usually in an autoclave so that the reaction mixture is subject to autogenous pressure. The reaction mixture can be stirred during crystallization.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as synthesized, SSZ-26 zeolite crystals. The drying step can be performed at atmospheric or subatmospheric pressures.

During the hydrothermal crystallization step, the SSZ-26 crystals can be allowed to nucleate spontaneously from the reaction mixture. The reaction mixture can also be seeded with SSZ-26 crystals both to direct, and accelerate the crystallization, as well as to minimize the formation of undesired aluminosilicate contaminants. If the reaction mixture is seeded with SSZ-26 crystals, the concentration of the organic compound can be greatly reduced.

The synthetic SSZ-26 zeolites can be used as synthesized or can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica:alumina mole ratio. These methods may also include the use of $(NH_4)_2SiF_6$ or acidic ion-exchange resin treatment. The zeolite can also be steamed; steaming helps stabilize the crystalline lattice to attack from acids. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired. Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Ga, Cd, Pt, Pd, Ni, Co, Ti, Al, Sn, Fe and Co are particularly preferred.

The hydrogen, ammonium, and metal components can be exchanged into the zeolite. The zeolite can also be impregnated with the metals, or, the metals can be physically intimately admixed with the zeolite using standard methods known to the art. And, the metals can be occluded in the crystal lattice by having the desired metals present as ions in the reaction mixture from which the SSZ-26 zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253. Ion exchange can take place either before or after the zeolite is calcined.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to 820° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

The SSZ-26 aluminosilicate can be formed into a wide variety of physical shapes. Generally speaking, the zeolite can be in the form of a powder, a granule, or a molded product, such as extrudate having particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e., combined with it, tends to improve the conversion and selectivity of the catalyst in certain organic conversion processes. Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and the kaolins commonly known as Dixie, McNamee, Georgia and Florida clays or others in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, the SSZ-26 zeolites can be composited with porous matrix materials and mixtures of matrix materials such as silica, alumina, titania, magnesia, silica:alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The SSZ-26 zeolites can also be composited with other zeolites such as synthetic and natural faujasites (e.g., X and Y), erionites, and mordenites. They can also be composited with purely synthetic zeolites such as those of the ZSM, EU, FU, and NU series. The combination of zeolites can also be composited in a porous inorganic matrix.

SSZ-26 zeolites are useful in hydrocarbon conversion reactions. Hydrocarbon conversion reactions are chemical and catalytic processes in which carbon containing compounds are changed to different carbon containing compounds. Examples of hydrocarbon conversion reactions include catalytic cracking, hydrocracking, and olefin and aromatics formation reactions. The catalysts are useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., metaxylene), and disproportionating aromatics (e.g., toluene) to provide mixtures of benzene, xylenes and higher methylbenzenes. The SSZ-26 catalysts have high selectivity, and under hydrocarbon conversion conditions can provide a high percentage of desired products relative to total products.

SSZ-26 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and, in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such as platinum, include hydrogenation-dehydrogenation reactions, denitrogenation and desulfurization reactions.

SSZ-26 can be used in hydrocarbon conversion reactions with active or inactive supports, with organic or inorganic binders, and with and without added metals.

These reactions are well known to the art, as are the reaction conditions.

Using SSZ-26 catalyst which contains a hydrogenation promoter, heavy petroleum residual feedstocks, cyclic stocks and other hydrocrackate charge stocks can be hydrocracked at hydrocracking conditions including a temperature in the range of from 175° C. to 485° C., molar ratios of hydrogen to hydrocarbon charge from 1 to 100, a pressure in the range of from 0.5 to 350 bar, and a liquid hourly space velocity (LHSV) in the range of from 0.1 to 30.

The hydrocracking catalysts contain an effective amount of at least one hydrogenation catalyst (component) of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like.

The hydrogenation catalyst is present in an effective amount to provide the hydrogenation function of the hydrocracking catalyst, and preferably in the range of from 0.05 to 25% by weight.

The catalyst may be employed in conjunction with traditional hydrocracking catalysts, e.g., any aluminosilicate heretofore employed as a component in hydrocracking catalysts. Representative of the zeolitic aluminosilicates disclosed heretofore as employable as component parts of hydrocracking catalysts are Zeolite Y (including steam stabilized, e.g., ultra-stable Y), Zeolite X, Zeolite beta (U.S. Pat. No. 3,308,069), Zeolite ZK-20 (U.S. Pat. No. 3,445,727), Zeolite ZSM-3 (U.S. Pat. No. 3,415,736), faujasite, LZ-10 (U.K. Patent 2,014,970, June 9, 1982), ZSM-5-type zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolites, LZ-210-type zeolite and mixtures thereof. Traditional cracking catalysts containing amounts of $Na_2O$ less than about one percent by weight are generally preferred. The relative amounts of the SSZ-26 component and traditional hydrocracking component, if any, will depend at least in part, on the selected hydrocarbon feedstock and on the desired product distribution to be obtained therefrom, but in all instances an effective amount of SSZ-26 is employed. When a traditional hydrocracking catalyst (THC) component is employed the relative weight ratio of the THC to the SSZ-26 is generally between about 1:10 and about 500:1, desirably between about 1:10 and about 200:1, preferably between about 1:2 to about 50:1, and most preferably is between about 1:1 and about 20:1.

The hydrocracking catalysts are typically employed with an inorganic oxide matrix component which may be any of the inorganic oxide matrix components which have been employed heretofore in the formulation of hydrocracking catalysts including: amorphous catalytic inorganic oxides, e.g., catalytically active silica-aluminas, clays, silicas, aluminas, silica-aluminas, silica-zirconias, silica-magnesias, alumina-borias, alumina-titanias and the like and mixtures thereof. The traditional hydrocracking catalyst and SSZ-26 may be mixed separately with the matrix component and then mixed or the THC component and SSZ-26 may be mixed and then formed with the matrix component.

SSZ-26 can be used to dewax hydrocarbonaceous feeds by selectively removing straight chain paraffins. The catalytic dewaxing conditions are dependent in large measure on the feed used and upon the desired pour point. Generally, the temperature will be between about 200° C. and about 475° C., preferably between about 250° C. and about 450° C. The pressure is typically between about 15 psig and about 3000 psig, preferably between about 200 psig and 3000 psig. The liquid hourly space velocity (LHSV) preferably will be from 0.1 to 20, preferably between about 0.2 and about 10.

Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling about 350° F.

The SSZ-26 hydrodewaxing catalyst may optionally contain a hydrogenation component of the type commonly employed in dewaxing catalysts. The hydrogenation component may be selected from the group of hydrogenation catalysts consisting of one or more metals of Group VIB and Group VIII, including the salts, complexes and solutions containing such metals. The preferred hydrogenation catalyst is at least one of the group of metals, salts and complexes selected from the group consisting of at least one of platinum, palladium, rhodium, iridium and mixtures thereof or at least one from the group consisting of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like.

The hydrogenation component is present in an effective amount to provide an effective hydrodewaxing catalyst preferably in the range of from about 0.05 to 5% by weight.

SSZ-26 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with the zeolite at a temperature in the range of from about 400° C. to 600° C., preferably 480° C.–550° C. at pressures ranging from atmospheric to 10 bar, and liquid hourly space velocities (LHSV) ranging from 0.1 to 15.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

The zeolite/Group VIII metal conversion catalyst can be used without a binder or matrix. The preferred inorganic matrix, where one is used, is a silica-based binder such as Cab-O-Sil or Ludox. Other matrices such as magnesia and titania can be used. The preferred inorganic matrix is nonacidic.

It is critical to the selective production of aromatics in useful quantities that the conversion catalyst be substantially free of acidity, for example, by poisoning the zeolite with a basic metal, e.g., alkali metal, compound. The zeolite is usually prepared from mixtures containing alkali metal hydroxides and thus have alkali metal contents of about 1–3 weight percent. These high levels of alkali metal, usually sodium, potassium or cesium, are unacceptable for most catalytic applications because they greatly deactivate the catalyst for cracking reactions. Usually, the alkali metal is removed to low levels by ion-exchange with hydrogen or ammonium ions. By alkali metal compound as used herein is meant elemental or ionic alkali metals or their basic compounds. Surprisingly, unless the zeolite itself is substantially free of acidity, the basic compound is required in the present process to direct the synthetic reactions to aromatics production.

The amount of alkali metal necessary to render the zeolite substantially free of acidity can be calculated using standard techniques based on the aluminum content of the zeolite. Under normal circumstances, the zeolite as prepared and without ion-exchange will contain sufficient alkali metal to neutralize the acidity of the catalyst. If a zeolite free of alkali metal is the starting material, alkali metal ions can be ion exchanged into the zeolite to substantially eliminate the acidity of the zeolite. An alkali metal content of about 100%, or greater, of the acid sites calculated on a molar basis is sufficient.

Where the basic metal content is less than 100% of the acid sites on a molar basis, the test described in U.S. Pat. No. 4,347,394 which patent is incorporated totally herein by reference, can be used to determine if the zeolite is substantially free of acidity.

The preferred alkali metals are sodium, potassium, and cesium. The zeolite itself can be substantially free of acidity only at very high silica:alumina mol ratios; by "zeolite consisting essentially of silica" is meant a zeolite which is substantially free of acidity without base poisoning.

Hydrocarbon cracking stocks can be catalytically cracked in the absence of hydrogen using SSZ-26 at liquid hourly space velocities from 0.5 to 50, temperatures from about 260° F. to 1625° F. and pressures from subatmospheric to several hundred atmospheres, typically from about atmospheric to about 5 atmospheres.

For this purpose, the SSZ-26 catalyst can be composited with mixtures of inorganic oxide supports as well as traditional cracking catalyst.

The catalyst may be employed in conjunction with traditional cracking catalysts, e.g., any aluminosilicate heretofore employed as a component in cracking catalysts. Representative of the zeolitic aluminosilicates disclosed heretofore as employable as component parts of cracking catalysts are Zeolite Y (including steam stabilized chemically modified, e.g., ultra-stable Y), Zeolite X, Zeolite beta (U.S. Pat. No. 3,308,069), Zeolite ZK-20 (U.S. Pat. No. 3,445,727), Zeolite ZSM-3 (U.S. Pat. No. 3,415,736), faujasite, LZ-10 (U.K. Patent No. 2,014,970, June 9, 1982), ZSM-5-type zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolites, LZ-210-type zeolite and mixtures thereof. Traditional cracking catalysts containing amounts of $Na_2O$ less than about one percent by weight are generally preferred. The relative amounts of the SSZ-26 component and traditional cracking component, if any, will depend at least in part, on the selected hydrocarbon feedstock and on the desired product distribution to be obtained therefrom, but in all instances an effective amount of SSZ-26 is employed. When a traditional cracking catalyst (TC) component is employed the relative weight ratio of the TC to the SSZ-26 is generally between about 1:10 and about 500:1, desirably between about 1:10 and about 200:1, preferably between about 1:2 and about 50:1, and most preferably is between about 1:1 and about 20:1.

The cracking catalysts are typically employed wit an inorganic oxide matrix component which may be any of the inorganic oxide matrix components which have been employed heretofore in the formulation of FCC catalysts including: amorphous catalytic inorganic oxides, e.g., catalytically active silica-aluminas, clays, silicas, aluminas, silica-aluminas, silica-zirconias, silica-magnesias, alumina-borias, alumina-titanias and the like and mixtures thereof. The traditional cracking component and SSZ-26 may be mixed separately with the matrix component and then mixed or the TC component and SSZ-26 may be mixed and then formed with the matrix component.

The mixture of a traditional cracking catalyst and SSZ-26 may be carried out in any manner which results in the coincident presence of such in contact with the crude oil feedstock under catalytic cracking conditions. For example, a catalyst may be employed containing the traditional cracking catalyst and a SSZ-26 in single catalyst particles or SSZ-26 with or without a matrix component may be added as a discrete component to a traditional cracking catalyst. SSZ-26 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerizaton process comprises contacting the olefin feedstock in the gaseous state phase with SSZ-26 at a temperature of from about 450° F. to about 1200° F., a WHSV of from about 0.2 to about 50 and a hydrocarbon partial pressure of from about 0.1 to about 50 atmospheres.

Also, temperatures below about 450° F. may be used to oligomerize the feedstock, when the feedstock is in the liquid phase when contacting the zeolite catalyst. Thus, when the olefin feedstock contacts the zeolite catalyst in the liquid phase, temperatures of from about 50° F. to about 450° F., and preferably from 80° to 400° F. may be used and a WHSV of from about 0.05 to 20 and preferably 0.1 to 10. It will be appreciated that the pressures employed must be sufficient to maintain the system in the liquid phase. As is known in the art, the pressure will be a function of the number of carbon atoms of the feed olefin and the temperature. Suitable pressures include from about 0 psig to about 3000 psig.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity of from about 0.1 to about 120, preferably from about 0.1 to about 100, as measured by its ability to crack n-hexane.

Alpha value are defined by a standard test known in the art, e.g., as shown in U.S. Pat. No. 3,960,978 which is incorporated totally herein by reference. If required, such zeolites may be obtained by steaming, by use in a conversion process or by any other method which may occur to one skilled in this art.

SSZ-26 can be used to convert light gas $C_2$–$C_6$ paraffins and/or olefins to higher molecular weight hydrocarbons including aromatic compounds. Operating temperatures of 100° C.–700° C., operating pressures of 0 to 1000 psig and space velocities of 0.5–40 hr$^{-1}$ WHSV (weight hourly space velocity) can be used to convert the $C_2$–$C_6$ paraffin and/or olefins to aromatic compounds. Preferably, the zeolite will contain a catalyst metal or metal oxide wherein said metal is selected from the group consisting of Group IB, IIB, VIII and IIIA of the Periodic Table, and most preferably gallium or zinc and in the range of from about 0.05 to 5% by weight.

SSZ-26 can be used to condense lower aliphatic alcohols having 1 to 10 carbon atoms to a gasoline boiling point hydrocarbon product comprising mixed aliphatic and aromatic hydrocarbon. The condensation reaction proceeds at a temperature of about 500° F. to 1000° F., a pressure of about 0.5 to 1000 psig and a space velocity of about 0.5 to 50 WHSV. The process disclosed in U.S. Pat. No. 3,984,107 more specifically describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals the cation content should in no case be so large as to effectively inactivate the catalyst.

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst with a hydrocarbon feed under isomerization conditions. The feed is preferably a light straight run fraction, boiling within the range of 30° F. to 250° F. and preferably from 60° F. to 200° F. Preferably, the hydrocarbon feed for the process comprises a substantial amount of $C_4$ to $C_7$ normal and slightly branched low octane hydrocarbons, more preferably $C_5$ and $C_6$ hydrocarbons.

The pressure in the process is preferably between 50 psig and 1000 psig, more preferably between 100 and 500 psig. The liquid hourly space velocity (LHSV) is preferably between about 1 to about 10 with a value in the range of about 1 to about 4 being more preferred. It is also preferable to carry out the isomerization reaction in the presence of hydrogen. Preferably, hydrogen is added to give a hydrogen to hydrocarbon ratio ($H_2$/HC) of between 0.5 to 10 $H_2$/HC, more preferably between 1 and 8 $H_2$/HC. The temperature is preferably between about 200° F. and about 1000° F., more preferably between 400° F. and 600° F. As is well known to those skilled in the isomerization art, the initial selection of the temperature within this broad range is made primarily as a function of the desired conversion level considering the characteristics of the feed and of the catalyst. Thereafter, to provide a relatively constant value for conversion, the temperature may have to be slowly increased during the run to compensate for any deactivation that occurs.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. An example of a suitable catalyst for this hydrodesulfurization process is an alumina-containing support and a minor catalytic proportion of molybdenum oxide, cobalt oxide and/or nickel oxide. A platinum on alumina hydrogenating catalyst can also work. In which case a sulfur sorber is preferably placed downstream of the hydrogenating catalyst, but upstream of the present isomerization catalyst. Examples of sulfur sorbers are alkali or alkaline earth metals on porous refractory inorganic oxides, zinc, etc. Hydrodesulfurization is typically conducted at 315° C. to 455° C., at 200 to 2000 psig, and at a liquid hourly space velocity of 1 to 5.

It is preferable to limit the nitrogen level and the water content of the feed. Catalysts and processes which are suitable for these purposes are known to those skilled in the art.

After a period of operation the catalyst can become deactivated by sulfur or coke. Sulfur and coke can be removed by contacting the catalyst with an oxygen-containing gas at an elevated temperature. If the Group VIII metal(s) have agglomerated, then it can be redispersed by contacting the catalyst with a chlorine gas under conditions effective to redisperse the metal(s). The method of regenerating the catalyst may depend on whether there is a fixed bed, moving bed, or fluidized bed operation. Regeneration methods and conditions are well known in the art.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

SSZ-26 can be used in a process for the alkylation or transalkylation of an aromatic hydrocarbon. The process comprises contacting the aromatic hydrocarbon with a $C_2$ to $C_4$ olefin alkylating agent or a polyalkyl aromatic hydrocarbon transalkylating agent, under at least partial liquid phase conditions, and in the presence of a catalyst comprising SSZ-26.

For high catalytic activity, the SSZ-26 zeolite should be predominantly in its hydrogen ion form. Generally, the zeolite is converted to its hydrogen form by ammonium exchange followed by calcination. If the zeolite is synthesized with a high enough ratio of organo-nitrogen cation to sodium ion calcination alone may be sufficient. It is preferred that, after calcination, at least 80% of the cation sites are occupied by hydrogen ions and/or rare earth ions.

The pure SSZ-26 zeolite may be used as a catalyst, but generally it is preferred to mix the zeolite powder with an inorganic oxide binder such as alumina, silica, silica/alumina, or naturally occurring clays and form the mixture into tablets or extrudates. The final catalyst may contain from 1 to 99 wt % SSZ-26 zeolite. Usually the zeolite content will range from 10 to 90 wt %, and more typically from 60 to 80 wt %. The preferred inorganic binder is alumina. The mixture may be formed into tablets or extrudates having the desired shape by methods well known in the art.

Examples of suitable aromatic hydrocarbon feedstocks which may be alkylated or transalkylated by the process of the invention include aromatic compounds such as benzene, toluene and xylene. The preferred aromatic hydrocarbon is benzene. Mixtures of aromatic hydrocarbons may also be employed.

Suitable olefins for the alkylation of the aromatic hydrocarbon are those containing 2 to 4 carbon atoms, such as ethylene, propylene, butene-1, transbutene-2 and cis-butene-2, or mixtures thereof. The preferred olefin is propylene. These olefins may be present in admixture with the corresponding $C_2$ to $C_4$ paraffins, but it is preferable to remove any dienes, acetylenes, sulfur compounds or nitrogen compounds which may be present in the olefin feedstock stream, to prevent rapid catalyst deactivation.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

Reaction products which may be obtained include ethylbenzene from the reaction of benzene with either ethylene or polyethylbenzenes, cumene from the reaction of benzene with propylene or polyisopropylbenzenes, ethyltoluene from the reaction of toluene with ethylene or polyethyltoluenes, cymenes from the reaction of toluene with propylene or polyisopropyltoluenes, and secbutylbenzene from the reaction of benzene and n-butenes or polybutylbenzenes. The production of cumene from the alkylation of benzene with propylene or the transalkylation of benzene with di-isopropylbenzene is especially preferred.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F., preferably, 250° F. to 450° F. The reaction pressure should be sufficient to maintain at least a partial liquid phase in order to retard catalyst fouling. This is typically 50 to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F., but it is preferably about 250° F. to 450° F. The reaction pressure should be sufficient to maintain a least a partial liquid phase, typically in the range of about 50 psig to 1000 psig, preferably 300 psig to 600 psig. The weight hourly space velocity will range from about 0.1 to 10.

SSZ-26 can also be used as an adsorbent, as a filler in paper, paint, and toothpastes, and as a water-softening agent in detergents.

The present invention will be more fully understood by reference to the following examples. They are intended to be purely exemplary and are not intended to limit the scope of the invention in any way.

EXAMPLES

Example 1

[4.3.3.0] Propellane-8,11-dione was prepared according to the Cook and Weiss [J. Org. Chem. 41 4053 (1976)]. The dione was then heated for 16 hours in a closed pressure vessel with Dimethylformamide and Formic acid (88%) in a Leukart-type reaction. The reaction is cooled to room temperature, dissolved in water, brought to a pH of 12 with alkali, and extracted twice with equal volumes of diethyl ether. The extract is dried over sodium sulfate and the solvent removed. The N,N,N', N'-tetramethyl [4.3.3.0] propellane-8,11-diamine product (which has an elemental analysis consistent with the theoretical structure of the diamine) is dissolved in chloroform and an excess of methyl iodide is added and the reaction is stirred overnight to produce the crystalline diquaternary ammonium product (a small amount of mono amine is also produced in this reaction sequence. It can be carried through all steps without adversely effecting the zeolite synthesis or can be removed by fractional crystallization from hot ethanol once the quaternized product has been achieved). The crystalline product having a melting point of 304°–306° C. is N,N,N,N',N',N'-Hexamethyl [4.3.3.0] Propellane-8,11-diammonium diiodide. At this stage three isomeric forms of the compound may be possible. The orientation of the diammonium groups relative to the carbocyclic skeleton may be syn,syn or syn,anti, or anti,anti. The template can be further purified by recrystallization from Ethanol/water (20/1). This greatly diminishes the formation of other zeolite impurities.

Example 2

The product of Example 1 was dissolved in water (so as to produce a 0.5 to 1.0M solution) and stirred overnight with an excess of Dowex 1 AG-X8 hydroxide ion-exchange resin. The resin was filtered and the basic solution was titrated with an analytical solution of HCl.

Similarly, other anions such as acetate, sulfate, bromide, carboxylate and tetrafluoroborate may be substituted for the hydroxy by using the appropriate ion-exchange resin.

Example 3

76 Grams of a 0.45M solution of Template from Example 2 in its hydroxide form were mixed with 1.58 gms of NaOH (solid). After dissolution 0.89 gm of sodium aluminate (75% solids) were added with stirring using a magnetic stir bar. Finally 9.08 gms of Cabosil M5 fumed silica was added. The reactants were loaded into a Parr 300 cc reactor, sealed and heated. The reactor was stirred at 60 RPM while being heated at 175° C. for 6 days. The product after filtration, washing with distilled water, drying in air and then at 100° C. was the crystalline material designated SSZ-26. The X-ray diffraction pattern of the as-made material is tabulated in Table 3 below.

TABLE 3

| 2 θ | d/n | 100 × I/I$_o$ | Comments |
|---|---|---|---|
| 7.83 | 11.300 | 100 | |
| 14.19 | 6.240 | 5 | |
| 15.65 | 5.660 | 7 | |
| 20.28 | 4.380 | 61 | |
| 20.93 | 4.240 | 9 | QTZ |
| 21.39 | 4.150 | 25 | |
| 22.00 | 4.040 | 55 | |
| 22.82 | 3.900 | 45 | Sh |
| 23.05 | 3.860 | 70 | |
| 25.26 | 3.530 | 9 | |
| 26.50 | 3.360 | 36 | |
| 26.68 | 3.340 | 54 | QTZ |

QTZ = Quartz
Sh = Shoulder

Example 4

75 Grams of a 0.45M solution of Template were mixed with 1.70 gms NaOH(s), and 2.70 gms of SK-40 Y zeolite (sold by Union Carbide) as source of alumina. After thorough mixing 7.20 gms of Cabosil was blended in as silica source. The reaction mixture was heated in a Parr 300 cc reactor at 175° C. at 45 RPM for 6 days. Workup as in Example 3 produced crystalline SSZ-26 and a minor amount of quartz.

Example 5

In this example Na-Y zeolite (SK-40) was used again but the initial OH$^-$/SiO$_2$ ratio was lowered to 0.20, 0.28 gms of SK-40, as source of alumina, was used and dispersed in 6 ml H$_2$O, 0.07 gm NaOH, and 2.4 gms of a 0.5M Template solution. 0.72 Grams of Cabosil was used and the reaction was run at 170° C. but at 30 RPM. At 6 days of reaction the product was crystalline SSZ-26. The SiO$_2$/Al$_2$O$_3$ value of the zeolite is 35.

Example 6

2.4 Grams of a 0.5M solution of Template was mixed with 6 ml of H$_2$O, 0.21 gms of NaOH(s), 0.29 gms of Na-Y zeolite, as source of alumina, and finally 0.72 gms of Cabosil M5. The mixture was heated at 160° C. for 6 days with 30 RPM agitation. The crystalline product was SSZ-26 and has a SiO$_2$/Al$_2$O$_3$ ratio of 25.

Example 7

A reaction like Example 6 was set up again. This time the reactants were increased 15 fold. The mixture was seeded with a small quantity from Example 6, and heated static at 160° C. The crystalline product after 12 days of reaction and the usual workup was SSZ-26, with minor quantities of analcime and quartz.

Example 8

The template is prepared as described in Example 1, but instead of using Ethanol/water in the final recrystallization step, Acetonitrile/water is used (15/1). A lower yield of crystals are recovered but it gives a correct microanalysis for the desired product. Even though the integrations are correct for the various protons as seen in the NMR, the coupling constants are now markedly different. Also the IR pattern contains some new bands. Clearly a different isomer has been recovered from the potential mixture. This new product is converted to the hydroxide form as in Example 2. 1.2 mmoles of this form of the template in 7 ml of water are combined with 0.20 gms of NaOH(s), 0.28 gms of SK-40 zeolite, and finally 0.72 gms of Cabosil. A Teflon ball (¾in.) is placed in the reactor to aid in stirring. The reactor is tumbled at 30 RPM while being heated to 170° C. for 6 days. The product after the usual workup was well-crystallized SSZ-26. The data for the XRD analysis appears in Table 4. This example demonstrates that more than one isomeric conformation is capable of producing SSZ-26 in the present invention.

TABLE 4

| 2 θ | d/n | 100 × I/I$_o$ |
|---|---|---|
| 7.77 | 11.38 | 76 |
| 8.92 | 9.91 | 11 B |
| 9.42 | 9.39 | 8 B |
| 13.15 | 6.73 | 7 B |
| 14.10 | 6.28 | 4 |
| 14.77 | 6.00 | 6 B |
| 15.25 | 5.84 | 6 |
| 15.58 | 5.69 | 11 |
| 19.68 | 4.51 | 14 B. |
| 20.20 | 4.396 | 80 |
| 21.24 | 4.183 | 38 |
| 21.84 | 4.069 | 72 |
| 22.77 | 3.905 | 63 Sh |
| 22.92 | 3.880 | 100 |
| 25.12 | 3.545 | 10 |
| 26.50 | 3.363 | 51 |
| 28.38 | 3.145 | 6 |
| 28.86 | 3.094 | 8 |
| 30.33 | 2.947 | 7 |

B = Broad
Sh = Shoulder

Example 9

3.75 gms of the template prepared as in Example 2 (0.63M) is combined with 0.30 gms of NaOH(s) and 9.3 ml water. 0.53 gms of SK-40 are added and then 1.35 gms of Cabosil. After placing a Teflon-coated stir bar in the reactor it is sealed and heated at 170° C. for 6 days while tumbling at 30 RPM. The product after the usual workup was SSZ-26 and the XRD data appears in Table 5.

TABLE 5

| 2 θ | d/n | 100 × I/I$_o$ |
|---|---|---|
| 7.74 | 11.420 | 90 |

TABLE 5-continued

| 2θ | d/n | 100 × I/I₀ |
|---|---|---|
| 8.30 | 10.650 | 6 B |
| 8.88 | 9.960 | 10 B |
| 13.20 | 6.707 | 7 B |
| 14.08 | 6.290 | 6 |
| 15.22 | 5.821 | 9 B |
| 15.55 | 5.698 | 12 |
| 16.63 | 5.331 | 2 |
| 19.59 | 4.531 | 10 |
| 20.17 | 4.402 | 100 |
| 21.26 | 4.179 | 40 |
| 21.87 | 4.064 | 88 |
| 22.77 | 3.905 | 60 Sh |
| 22.92 | 3.880 | 100 |
| 25.14 | 3.542 | 14 |
| 26.45 | 3.370 | 60 |
| 27.62 | 3.230 | 4 B |
| 27.93 | 3.194 | 4 B |
| 28.43 | 3.139 | 11 |
| 28.90 | 3.089 | 10 |
| 29.60 | 3.018 | 3 B |
| 30.33 | 2.947 | 11 |
| 31.43 | 2.846 | 8 |
| 31.93 | 2.803 | 7 |
| 33.19 | 2.699 | 12 |
| 35.32 | 2.541 | 10 |
| 35.63 | 2.520 | 5 |
| 36.30 | 2.475 | 3 |
| 36.80 | 2.442 | 8 |
| 37.23 | 2.415 | 5 |
| 40.17 | 2.245 | 6 |
| 41.95 | 2.154 | 2 |
| 43.06 | 2.101 | 7 |

B = Broad
Sh = Shoulder

Example 10

1.2 mm of the template from Example 2 and in 8 ml water is combined with 0.12 gms of NaOH(s), 0.28 gms of SK-40, and finally 0.72 gms of Cabosil. After adding the Teflon-coated stirrer and closing the reactor, the reaction is run for about 9 days at 160° C. and 30 RPM tumbling. The product was a nicely crystallized sample of SSZ-26. The product showed a very homogeneous distribution in the scanning electron microscope. The XRD data is given in Table 6.

TABLE 6

| | As Prepared | |
|---|---|---|
| 2θ | d/n | 100 × I/I₀ |
| 7.78 | 11.36 | 100 |
| 8.32 | 10.63 | 4 B |
| 8.90 | 9.94 | 10 B |
| 13.20 | 6.71 | 5 |
| 14.15 | 6.26 | 5 |
| 15.26 | 5.81 | 4 B |
| 15.62 | 5.67 | 8 |
| 15.92 | 5.57 | 7 |
| 16.74 | 5.30 | 2 |
| 19.63 | 4.52 | 6 B |
| 20.23 | 4.389 | 63 B |
| 21.37 | 4.158 | 25 |
| 21.99 | 4.042 | 53 |
| 22.85 | 3.89 | 46 Sh |
| 23.00 | 3.867 | 64 |
| 25.20 | 3.534 | 9 |
| 26.15 | 3.408 | 8 |
| 26.49 | 3.365 | 33 |
| 28.51 | 3.131 | 8 |
| 28.95 | 3.084 | 7 |

B = Broad
Sh = Shoulder

Example 11

The crystalline products of Examples 3–10 were subjected to calcination as follows. The samples were heated in a muffle furnace from room temperature up to 540° C. at a steadily increasing rate over a 7-hour period. The samples were maintained at 540° C. for four more hours and then taken up to 600° C. for an additional four hours. A 50/50 mixture of air and nitrogen was passed over the zeolites at a rate of 20 standard cubic feet per minute during heating. Representative X-ray diffraction data for the calcined product of Example 8 appears in Table 7.

TABLE 7

| 2θ | d/n | 100 × I/I₀ | Comments |
|---|---|---|---|
| 6.18 | 14.300 | 3 | Y zeolite |
| 7.74 | 11.420 | 100 | |
| 8.30 | 10.650 | 3 | |
| 8.63 | 10.250 | 3 | |
| 8.95 | 9.880 | 6 | |
| 9.44 | 9.370 | 12 | |
| 9.82 | 9.007 | 6 | |
| 13.12 | 6.748 | 13 | |
| 14.08 | 6.290 | 10 | |
| 14.75 | 6.006 | 6 | |
| 15.53 | 5.706 | 9 | |
| 16.00 | 5.539 | 2 | |
| 16.63 | 5.331 | 5 | |
| 19.75 | 4.495 | 9 | |
| 20.18 | 4.400 | 60 | |
| 20.85 | 4.260 | 5 | QTZ |
| 21.27 | 4.177 | 21 | |
| 21.90 | 4.058 | 55 | |
| 22.90 | 3.883 | 49 | Sh |
| 23.03 | 3.862 | 98 | |
| 25.17 | 3.538 | 18 | |
| 26.45 | 3.370 | 58 | |
| 26.60 | 3.351 | 36 | QTZ |
| 28.42 | 3.140 | 12 | |
| 28.90 | 3.089 | 15 | |
| 29.63 | 3.015 | 4 | |
| 30.40 | 2.940 | 10 | |
| 31.41 | 2.848 | 8 | |
| 32.00 | 2.797 | 7 | |
| 33.27 | 2.693 | 11 | |
| 35.38 | 2.537 | 9 | |
| 35.62 | 2.520 | 4 | |
| 36.32 | 2.473 | 4 | |
| 39.79 | 2.443 | 5 | |
| 37.33 | 2.409 | 2 | |
| 38.32 | 2.349 | 4 | |
| 40.15 | 2.246 | 4 | |
| 42.00 | 2.151 | 1 | |
| 42.42 | 2.131 | 1 | |
| 43.76 | 2.069 | 7 | |

QTZ = Quartz
Sh = Shoulder

Example 12

Ion-exchange of the calcined SSZ-26 materials from Example 8 was carried out using $NH_4NO_3$ to convert the zeolites from their Na form to $NH_4$ and then eventually H form. Typically the same mass of $NH_4NO_3$ as zeolite was slurried into $H_2O$ at ratio of 50/1 $H_2O$ to zeolite. The exchange solution was heated at 100° C. for two hours and then filtered. This process was repeated four times. Finally, after the last exchange the zeolite was washed several times with $H_2O$ and dried. A repeat calcination as in Example 11 was carried out but without the final treatment at 600° C. This produces the H form of SSZ-26 zeolite.

Example 13

The product of Example 6, after sequential treatment as in Examples 11 and then 12, was subjected to a surface area and pore size distribution analysis using $N_2$ as adsorbate and via the BET method. The surface area of the zeolitic material was 560 $m^2/gm$ and the micropore volume was 0.19 cc/gm.

Example 14

Constraint Index Determination:

0.25 Grams of the hydrogen form of the zeolite of Example 4 (after treatment according to Examples 11 and 12) was packed into a ⅜" stainless steel tube with alundum on both sides of the zeolite bed. A Lindburg furnace was used to heat the reactor tube. Helium was introduced into the reactor tube at 10 cc/min. and atmospheric pressure. The reactor was taken to 250° F. for 40 min. and then raised to 600° F. Once temperature equilibration was achieved at 50/50, w/w feed of n-hexane and 3-methylpentane was introduced into the reactor at a rate of 0.62 cc/hr. Feed delivery was made via syringe pump. Direct sampling onto a gas chromatograph began after 10 minutes of feed introduction. The constraint index value was calculated from gas chromatographic data using methods known in the art. It can be seen that novel zeolite SSZ-26 has very high cracking activity.

| Example No. | C.I. | Conversion at 10 min. | Temp. °F. |
|---|---|---|---|
| 4 | 0.3 | 95% | 600 |

Example 15

SSZ-26 was prepared as in Example 9 and treated as in Examples 11 and 12. The acid form of the zeolite was then neutralized by refluxing overnight with dilute KOH. After washing and drying the zeolite it was calcined to 1000° F. The KOH treatment was repeated a second time with subsequent washing, drying and calcination. The K-exchanged zeolite was impregnated (via incipient wetness) with 0.8 wt. % Pt, dried overnight at 250° F. and then calcined 3 hours at 500° F. The catalyst was then evaluated using a light straight run feed. Reactor conditions:

100=psig
2=LHSV
3=$H_2$/HC
800° F.=Temp.

| Composition, Wt % | Feed | Product |
|---|---|---|
| $C_4-$ | 0.0 | 30.5 |
| Total $C_5$ | 4.2 | 12.7 |
| i $C_6$ | 11.3 | 11.8 |
| n $C_6$ | 17.0 | 4.9 |
| Benzene | 0.5 | 12.5 |
| i $C_7$ | 14.5 | 1.7 |
| n $C_7$ | 16.7 | 0.6 |
| Toluene | 2.4 | 16.9 |
| i $C_8+$ | 0.9 | 0.0 |
| n $C_8+$ | 4.9 | 0.6 |
| $C_8+$ Aromatics | 1.4 | 4.6 |
| LV % | 100 | 64.2 |
| RON | 62 | 88.3 |

As might be anticipated the liquid volume yield could be improved by further neutralization of the zeolite catalyst.

Example 16

The hydrogen form of SSZ-26 can be used in catalytic cracking. For such purposes, the catalyst prepared as in Example 9 was tested in a micro-activity test (MAT) using the procedure developed by ASTM Committee D-32. The test was run at 925° F. on fresh catalyst at a cat/oil ratio of 3 (based upon catalyst calcined to 1100° F.) and a WHSV of 15-16. Table 8 shows inspections on the feed and the resulting products. The catalyst was run at 20 weight % in a kaolin matrix.

TABLE 8

| MAT Test for SSZ-26 Zeolite | |
|---|---|
| Feed: | |
| API | 29.09 |
| Aniline pt, F | 219.1 |
| Ramsbottom Carbon, wt % | 0.3 |
| N(T), ppm | 270 |
| N(B), ppm | 159 |
| S(T), wt % | 0.54 |
| Test Data: | |
| Conversion, wt % | 61.0 |
| Coke, wt % | 7.8 |
| $C_5-430°$ F. | 23.0 |
| 403-650° F. | 16.0 |
| 650+ | 23.0 |
| $C_3-$ | 14.8 |
| $C_4-$ | 30.2 |
| $C_4$ olefin/$C_4$ total | 0.21 |

Example 17

The hydrogen form of the SSZ-26 zeolite can be used in hydrocracking conversions of hydrocarbon feeds. The data shown in Table 9 is for the conversion of a feed made up of representative model compounds. The data illustrates the high activity and shape-selectivity for SSZ-26 zeolite in hydroprocessing. The catalyst is active by itself as used in this example or when a noble metal is incorporated. One gram (dry basis) of catalyst was loaded into a ¼" reactor tube packed with alundum on either side of the bed. The catalyst was dried at 500° F. for 30 min. with 1200 psi $H_2$. The hydrogen flow rate is 55 cc/min. at atmospheric pressure and room temperature. The feed rate was 50 microliters/min. and the catalyst was equilibrated for 2 hours at temperature before G.C. analysis.

TABLE 9

| | Hydroprocessing of a Model Feed With SSZ-26 Zeolite | | |
|---|---|---|---|
| Catalyst | Feed Alone | SSZ-26 | SSZ-26 |
| Temp. | — | 500° F. | 600° F. |
| LHSV | | | |
| $H_2$ Pressure | | 1200 | 1200 |
| Conversion | | 22.6 | 37.5 |
| Product/Feed wt % | | | |
| $C_1$—$C_6$ | 0.0 | 20.0 | 33.1 |
| Hexamethylethane Marker | 1.1 | 1.6 | 1.8 |
| Cyclohexane | 31.9 | 18.4 | 9.0 |
| Isooctane(2,2,4) | 4.5 | 4.0 | 3.9 |
| Toluene | 33.7 | 33.1 | 31.2 |
| 3,4,Diethyl $C_6$ | | | |
| 4-Propyl heptane | 10.1 | 11.7 | 12.2 |
| n-Decane | 5.1 | 2.6 | 0.7 |
| t-Decalin | 5.5 | 4.9 | 3.7 |
| c-Decalin | 4.5 | 0 | 0 |

TABLE 9-continued

| Catalyst | Hydroprocessing of a Model Feed With SSZ-26 Zeolite | | |
|---|---|---|---|
| | Feed Alone | SSZ-26 | SSZ-26 |
| n-Dodecane | 3.7 | 1.1 | 0 |

As can be seen above the catalyst has surprising selectivity for n-paraffins, demonstrating its usefulness for dewaxing, and a selectivity for cis decalin over the trans isomer. The reactivity is also somewhat pressure dependent.

Example 18

Due to the strong cracking activity of the SSZ-26 zeolite it can be advantageously used in the isomerization of pen-hex streams to upgrade octane values. Hydrogen SSZ-26 was prepared as in Examples 9, 11, and 12 and was impregnated with 0.8 wt % platinum. Pure hexane was run over the catalyst using the following parameters:
  100 psig
  6=$H_2$/HC
  3=LHSV
  501° F.=Temp.

The product distribution from the reaction is given in Table 10.

TABLE 10

| Hydrocarbon | Wt % |
|---|---|
| Methane | 0.12 |
| Ethane | 0.21 |
| Propane | 1.29 |
| Isobutane | 1.05 |
| n-Butane | 0.45 |
| Isopentane | 1.37 |
| n-Pentane | 0.65 |
| 2,2 DM Butane | 15.74 |
| 2,3, DM Butane | 8.66 |
| 2,Methylpentane | 31.80 |
| 3,Methylpentane | 20.99 |
| n-Hexane | 17.51 |
| Me,Cyclopentane | 0.17 |
| Benzene | 0.0 |
| LV % | 96.9 |
| RON | 75.7 |

Example 19

A commercial pen-hex stream, characterized below, was used with a 0.3% Pt catalyst prepared similarly to the one used in Example 18, and the catalyst run conditions were:
  200=psig
  6=$H_2$/HC
  1=LHSV
  485° F.=Temp.

At 22 hours on stream the product was the following:

| Hydrocarbon | Feed, Wt % | Product Wt % |
|---|---|---|
| Methane | 0.0 | 0.0 |
| Ethane | 0.0 | 0.0 |
| Propane | 0.0 | 1.81 |
| Isobutane | 0.04 | 6.49 |
| n-Butane | 0.28 | 1.15 |
| Isopentane | 12.03 | 22.40 |
| n-Pentane | 18.93 | 11.75 |
| 2,2, DM Butane | 0.58 | 5.09 |
| Cyclopentane | 4.26 | 3.96 |
| 2,3 DM Butane | 2.26 | 4.48 |
| 2,Methylpentane | 12.55 | 15.14 |
| 3,Methylpentane | 8.19 | 9.81 |
| n-Hexane | 19.74 | 8.33 |
| Me,Cyclopentane | 15.04 | 6.58 |
| Benzene | 3.75 | 0.00 |
| Cyclohexane | 1.89 | 1.91 |
| Isoheptane | 0.07 | 1.11 |
| n-Heptane | 0.15 | 0.00 |
| Toluene | 0.00 | 0.00 |
| LV % | 100 | 93.0 |
| RON(GC) | 74.5 | 79.8 |

Example 20

The SSZ-26 zeolite catalyst can be used for hydrocracking in conjunction with a metal component and under hydrogen. The zeolite of Example 9 was treated as in Examples 11 and 12 to produce the acidic form. About 0.6 wt % Pd was loaded onto the zeolite by ion-exchange in a buffered (pH 9.5) solution. Calcination was carried out in steps to 940° F. where the product is held for 3 hours. Next the zeolite was bound in Catapal alumina (65/35) and meshed to 24–40. The experimental conditions and product properties are given in the tables below.

After hydrogen reduction at 600° F. and titration at 350° F. with Feed A (see Table 11) spiked with 800 ppm N using n-butylamine, Feed A was hydrocracked over the catalyst under the conditions given in Table 12. The product properties are given in Table 13.

TABLE 11

| Properties of Feed A | |
|---|---|
| Nitrogen, ppm | 0.3 |
| Sulfur, ppm | ~2 |
| API Gravity | 32.0 |
| Boiling Range, °F. | |
| 0–5% | 454–544 |
| 5–50% | 544–716 |
| 50–90% | 716–834 |
| 85–100% | 866–919 |

TABLE 12

| Run Conditions For Hydrocracking Feed A with Catalyst Pd H SSZ-26 | |
|---|---|
| Temperature, °F. | 550 |
| WHSV | 1.53 |
| Total Pressure, psig | 1185 |
| Inlet $H_2$ P, psia | 1129 |
| Gas Rate, SCFB | 5707 |

TABLE 13

| Properties of Hydrocracked Product From Feed A Using the Catalyst Under Conditions Given in Table 12 | |
|---|---|
| Conversion to 450° F.-, Wt % | 71.5 |
| $C_5$+ Yield, Wt % | 83.0 |
| $C_5$ —180° F. Yield, Wt % | 23.6 |
| 180–390° F., Wt % | 29.9 |
| 390–450° F., Wt % | 0.5 |
| Chem $H_2$ Consumed, SCFB | 936 |
| Boiling Range, °F. | |
| 0–5% | 41–79 |
| 5–50% | 79–256 |
| 50–70% | 256–599 |
| 70–90% | 599–778 |
| 95–99% | 822–890 |

Example 21

The ability of the SSZ-26 zeolite to catalyze the alkylation of an aromatic hydrocarbon by an olefin was demonstrated as follows. SSZ-26 powder from Example 4 after treatment as in Examples 11 and 12 was pressed to form tablets which were crushed and sieved to obtain 10–20 mesh granules for testing. The granular catalyst was calcined for 4 hours at 1000° F. in a muffle furnace, then weighed and charged to a tubular microreactor. The catalyst was heated to 325° F. in flowing nitrogen at atmospheric pressure. Nitrogen flow continued while the reactor was pressurized to 600 psig. When the unit pressure had stabilized at 600 psig, the nitrogen flow was stopped and liquid benzene was passed upflow through the reactor. After the reactor was filled with liquid benzene, liquid propylene was injected into the benzene feed stream to given benzene/propylene feed molar ratio of 7.2 and a total feed rate of 5.7 grams per gram of catalyst per hour.

Analysis of the reactor effluent by capillary gas-liquid-chromatography showed that all of the propylene had been converted to make a product comprising 93.5% cumene and 5.9% diisopropylbenzenes on a benzene free weight basis. Since SSZ-26 is also a good transalkylation catalyst, it is anticipated that the diisopropylbenzene would be either recycled to the alkylation reactor or reacted in a separate reactor with benzene to make additional cumene. The conversion to useful product was thus better than 99 weight percent based on propylene and benzene reacted.

What is claimed is:

1. A zeolite having a mole ratio of an oxide selected from silicon oxide, germanium oxide and mixtures thereof to an oxide selected from aluminum oxide, gallium oxide, iron oxide, and mixtures thereof greater than about 10:1, and having the X-ray diffraction lines of Table 1.

2. A zeolite having a composition, as synthesized and in the anhydrous state, in terms of mole ratios of oxides as follows: (0.1 to 2.0)Q$_2$O:(0.1 to 2.0)M$_2$O:W$_2$O$_3$: (greater than 10) YO$_2$ wherein M is an alkali metal cation, W is selected from aluminum, gallium, iron and mixtures thereof, Y is selected from silicon, germanium and mixtures thereof, Q is a hexamethyl[4.3.3.0]propellane-8,11-diammonium cation and having the X-ray diffraction lines of Table 1.

3. The zeolite according to claim 2 wherein W is aluminum and Y is silicon.

4. A zeolite prepared by thermally treating the zeolite of claim 2 at a temperature from about 200° C. to 820° C.

5. The zeolite according to claim 4 having the X-ray diffraction lines of Table 2.

6. The zeolite according to claim 1 or 2 wherein said mole ratio of silicon oxide or germanium oxide to aluminum oxide, gallium oxide, or iron oxide is about 10:1 to 200:1.

7. A zeolite according to claim 1, 2 or 4 which has undergone ion exchange with hydrogen, ammonium, rare earth metal, Group IIA metal, or Group VIII metal ions.

8. A zeolite according to claim 1, 2 or 4 wherein rare earth metals, Group IIA metals, or Group VIII metals are occluded in the zeolite.

9. A zeolite composition, comprising the zeolite of claim 1, 2 or 4 and an inorganic matrix.

10. A method for preparing the zeolite of claim 1, comprising:
   (a) preparing an aqueous mixture containing sources of an alkali metal oxide, a hexamethyl[4.3.3.0]propellane-8,11-diammonium cation, an oxide selected from aluminum oxide, gallium oxide, iron oxide and mixtures thereof, and an oxide selected from silicon oxide, germanium oxide, and mixtures thereof;
   (b) maintaining the mixture at a temperature of at least 140° C. until the crystals of said zeolite form; and
   (c) recovering said crystals.

11. The method according to claim 10 wherein the aqueous mixture has a composition in terms of mole ratios of oxides falling in the ranges: YO$_2$/W$_2$O$_3$, 10:1 to 200:1; Q/YO$_2$, 0.05:1 to 0.50:1; wherein Y is selected from silicon, germanium and mixtures thereof, W is selected from aluminum, gallium, iron and mixtures thereof, and Q is a hexamethyl[4.3.3.0]propellane-8,11-diammonium cation.

12. The method according to claim 10 or 11 wherein Y is silicon and W is aluminum.

* * * * *